United States Patent [19]

Farhadieh

[11] 4,025,654
[45] May 24, 1977

[54] STABLE CHELOCARDIN COMPOSITION

[75] Inventor: Bahram Farhadieh, Libertyville, Ill.

[73] Assignee: Abbott Laboratories, North Chicago, Ill.

[22] Filed: Dec. 17, 1975

[21] Appl. No.: 641,408

Related U.S. Application Data

[63] Continuation-in-part of Ser. No. 566,596, April 9, 1975, abandoned.

[52] U.S. Cl. .............................. 424/330; 424/122
[51] Int. Cl.² ..................................... A61K 31/135
[58] Field of Search ........................... 424/122, 330

[56] References Cited

UNITED STATES PATENTS 3,155,582   11/1964   Oliver et al. .................. 424/122

OTHER PUBLICATIONS

Gregory, "Uses & Applications of Chemicals & Related Materials," (1939), p. 534, Reinhold Pub. Corp.

*Primary Examiner*—V. D. Turner
*Attorney, Agent, or Firm*—Paul D. Burgauer; Robert L. Niblack

[57] ABSTRACT

A dry chelocardin salt composition which is stable to extended storage periods comprises a mixture of monosodium chelocardin and between 0.2 and 2.0 parts of sodium citrate.

5 Claims, No Drawings

STABLE CHELOCARDIN COMPOSITION

HISTORY OF THIS APPLICATION

This application is a continuation in part of my earlier filed application Ser. No. 566,596, filed on Apr. 9, 1975, now abandoned.

DETAILED DESCRIPTION OF THE INVENTION

Chelocardin is the antibiotic described in U.S. Pat. No. 3,155,582; it was originally identified by M-319, but since that time its chemical structure has been determined; it is a tetracyclic compound carrying specific functional groups in various positions:

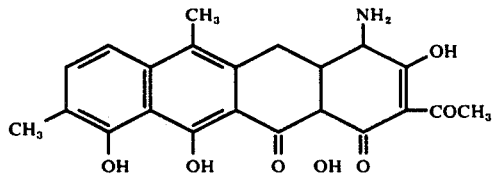

The primary use for this antibiotic lies in its form as a parenteral solution; it shows outstanding activity against numerous bacteria not affected by other antibacterial drugs.

Unfortunately, however, chelocardin as a base or in the form of an acid addition salt is insoluble in water. This means that chelocardin base or, for instance its hydrochloride salt, cannot be used for making injectable solutions. On the other hand, alkaline salts of chelocardin are so highly unstable that they are of no practical value in the drug field; they degrade promptly and lose their antibacterial activity even when stored in the cold and under a nitrogen atmosphere.

It is therefore an object of the present invention to make a reconstitutable, water soluble solid product containing chelocardin activity; it is a particular object of this invention to produce a solid composition that can readily be converted into an injectable solution and, at the same time, is stable to storage.

These and other objects are accomplished by providing a composition, in dry, solid form of a lyopholized mixture consisting essentially of 1 part of the monosodium salt of chelocardin and between 0.2 and 2 parts by weight of sodium citrate. A freeze-dried composition of this nature can be stored almost indefinitely under proper storage conditions. All reference to sodium citrate herein is intended to indicate the dry sodium salt of citric acid.

The findings covered by the present invention are very unusual and unexpected, paticularly because (a) chelocardin base or its salts with organic or inorganic acids are water insoluble and unsuitable for the in situ reconstitution into an injectable form, and (b) alkaline metal salts of chelocardin are completely unstable and thus totally unsuitable for use as a drug component for the preparation of injectable solutions. For instance, the sodium salt of chelocardin referred to above is so unstable that even under most cautious storage conditions it loses its potency and antibiotic activity to a great extent within a short period of time. It is also surprising to find that among all possible additives ordinarily used in preparations of this type, only sodium citrate has the unique property of stabilizing the sodium chelocardin to the point of making it a reconstitutable powder or a composition that can be stored under ordinary, precautionary storage conditions. The new composition is well suited for the preparation of an injectable solution by the simple addition of water or a buffered aqueous medium.

In order to illustrate the results obtained with the present invention, reference is made to the following example which, however, is not meant to limit the invention in any respect.

EXAMPLE 1

To a solution of 5 g. of sodium citrate dihydrate in 200 ml. of water is added 5 g. of chelocardin hydrochloride and the mixture is stirred to disperse the latter in a solution. The dispersion is then cooled to 5° C. and neutralized by the addition of the stoichiometric quantity of sodium hydroxide (223 ml. of 0.1 N sodium hydroxide). The resulting amber colored solution has a pH of between 8.0 and 8.7; it is diluted by the addition of water to make a total volume of 500 ml. The solution is then distributed in vials, 10 ml. per vial, and freeze dried in an ordinary freeze dry apparatus which allows the closure of each vial without removing the vials from the apparatus. Upon termination of the freeze drying cycle, the vacuum in the apparatus is partially replaced by nitrogen to a pressure of about ½ atm. The vials are then sealed and ready for storage or use at any time.

When in the above example the sodium citrate is varied between 1 g. and 10 g. per 5 g. of chelocardin hydrochloride, the stability of the product is essentially the same as that of the above described composition.

The stability of the product of the above example as well as some comparative products are carried out by standard, accelerated stability test methods, through determination of the first order degradation rate constant, and the results are given in the following table.

| Degradation Rate Constants k (expressed in $10^5$/hr.) | | | |
|---|---|---|---|
| Average of various lots | at 60° C. | at 80° C. | at 100° C. |
| 1) Na-chelocardin | 44.6 | 167.3 | 595.1 |
| 2) Na-chelocardin + Na-citrate (1:1 by wt.) | 5.6 | 21.6 | 57.0 |

All of the above degradation constants were determined on 3 to 4 lots prepared and stored in identical fashion to the lyopholized product of the above example. Each of the above degradation rate constants is the average value of at least 3 lots each of which was based on at least 18 individual assays, taken continuously over a time period of at least 2 weeks.

From the above table, the projected rate constant at 25° was calculated by standard kinetic procedures. The product of line 1 shows a first order degradation rate constant of $2.6 \times 10^5$ per hour while the product according to the current invention (line 2) shows a constant of $0.47 \times 10^5$ per hour. By conversion in standard fashion, the constants just given can be expressed as a 10% degradation time at 25° C. showing that the product line 1 is reduced to 90% of initial activity in 0.47 years while the product of line 2 degrades to this level only after 2.5 years. The results shown and calculated above clearly shows the unexpected improvement obtained by the addition of sodium citrate. This result is particularly surprising in view of the fact that other commonly used stabilizers such as sodium ascorbate, sodium hydrosulfite, sodium formaldehyde-sulfoxylate and others do not produce the above improvement and in many instances, they are detrimental to the chelocardin stability.

The findings shown above and the calculation of degradation rate through standard kinetic formulas was confirmed by the values obtained by a 3-months stability study carried out under the above described conditions at 40° C.

EXAMPLE 2

In an effort to determine the effect of various amounts of sodium citrate on the stability of monosodium chelocardin, five 200-ml solutions containing 0.0, 1.0, 3.0, 5.0 and 7.5 g of sodium citrate (S.C.), respectively, are prepared. To each of these 5 g of chelocardin hydrochloride (Ch) is added, resulting in various S.C.-to-Ch ratios. All of the samples are treated with stoichiometric amounts of sodium hydroxide as described in Example 1 and the solutions are then placed in vials and lyophilized as above. The accelerated stability tests carried out at 100° C for 24 hrs and 48 hrs produce the following percent potency losses based on the initial potency:

| S.C./Ch Ratio | 24 hrs. | 48 hrs. |
| --- | --- | --- |
| 0 :1 | 24% | 35% |
| 0.2:1 | 10% | 15% |
| 0.6:1 | 2% | 5% |
| 1.0:1 | 1% | 2% |
| 1.5:1 | 0.0% | 1% |

The results in the above table show the drastic improvement attainable by the addition of specified amounts of sodium citrate to the monosodium salt of chelocardin. The accelerated stability test used in this example is a widely accepted method to determine long-term stability at room temperature or otherwise proper storage conditions.

While it has been pointed out above that sodium citrate amounts are flexible within a range of 20–200% by weight of the hydrochloride salt of chelocardin, it should be noted that these amounts are based on crystalline sodium citrate dihydrate, i.e., the most convenient form of that salt. Of course, other forms or hydrates thereof can be used as long as the equimolar amount is chosen to be within the described range. In the simplest and often preferred embodiment, equal weight parts of the two components are used where chelocardin is used in the form of the stable but water-insoluble chelocardin hydrochloride and sodium citrate dihydrate. Other acid addition salts of chelocardin can be used in place of the hydrochloride since that salt is neutralized by the addition of the necessary amount of sodium hydroxide. Since the hydrochloride salt used above and the monosodium salt of chelocardin differ in molecular weight by less than 3%, a stable composition can be made according to the present invention by basing the ratio of components on either form of chelocardin mentioned above.

The stable, reconstitutable mixture of the present invention readily dissolves in water. The preferred concentration for making such a solution is one that contains between 1 and 6 mg/ml. of the above solids. It is often preferred to add a suitable, pharmaceutically acceptable buffer to such a solution in order to achieve and maintain a pH of between 7.6 and 8.0 in order to prevent the chelocardin from precipitating and to maintain its stability from the time the solution is prepared until it is injected into the patient.

It will be obvious to those skilled in the art that the new composition may contain optional additives frequently used in the preparation of injectable solutions, e.g. preservatives, buffers and the like. In many instances, suitable pharmaceutically acceptable ingredients of this nature may be added to the above aqueous starting material before freeze-drying.

What is claimed is:

1. A solid, pharmaceutical antibiotic composition suitable for reconstitution into a parenteral solution consisting essentially of a freeze-dried mixture of monosodium chelocardin and sodium citrate dihydrate in a weight ratio of between 1:0.2 and 1:2.

2. The composition of claim 1 wherein said ratio is between 1:0.2 and 1:1.5.

3. The composition of claim 1 wherein said ratio is essentially 1:1.

4. The process of preparing a pharmaceutical composition according to claim 1 wherein a dispersion of a pharmaceutically acceptable salt of chelocardin is converted to the monosodium salt of chelocardin by the addition of a stoichiometric amount of sodium hydroxide, adding between 0.2 and 2 parts by weight of sodium citrate dihydrate per part of chelocardin and freeze-drying said mixture to a dry solid.

5. The process of claim 4 wherein said salt of chelocardin is the hydrochloride salt.

* * * * *